# United States Patent
Tek et al.

(10) Patent No.: US 8,170,304 B2
(45) Date of Patent: May 1, 2012

(54) MODELING CEREBRAL ANEURYSMS IN MEDICAL IMAGES

(75) Inventors: Huseyin Tek, Princeton, NJ (US); Mehmet Akif Gulsun, Lawrenceville, NJ (US)

(73) Assignee: Siemens Aktiengesellschaft, München (DE)

( * ) Notice: Subject to any disclaimer, the term of this patent is extended or adjusted under 35 U.S.C. 154(b) by 1176 days.

(21) Appl. No.: 11/953,142

(22) Filed: Dec. 10, 2007

(65) Prior Publication Data

US 2008/0249755 A1 Oct. 9, 2008

Related U.S. Application Data

(60) Provisional application No. 60/909,724, filed on Apr. 3, 2007.

(51) Int. Cl.
*G06K 9/00* (2006.01)

(52) U.S. Cl. ........................................ 382/128

(58) Field of Classification Search ................. 382/154, 382/128, 156, 168, 190, 250, 285; 715/383; 702/152, 153; 354/664
See application file for complete search history.

(56) References Cited

U.S. PATENT DOCUMENTS

| 6,370,414 | B1 * | 4/2002 | Robinson ..................... | 600/409 |
|---|---|---|---|---|
| 6,591,004 | B1 * | 7/2003 | VanEssen et al. ............. | 382/154 |
| 7,315,640 | B1 * | 1/2008 | Brady et al. .................. | 382/132 |
| 7,684,600 | B2 * | 3/2010 | Wang ............................ | 382/128 |
| 7,983,459 | B2 * | 7/2011 | Begelman et al. ............ | 382/128 |
| 2003/0056799 | A1 * | 3/2003 | Young et al. .................. | 128/922 |
| 2003/0068074 | A1 * | 4/2003 | Hahn ............................. | 382/128 |
| 2004/0086175 | A1 * | 5/2004 | Parker et al. .................. | 382/154 |
| 2005/0018900 | A1 * | 1/2005 | Bruijns ......................... | 382/154 |
| 2005/0041842 | A1 * | 2/2005 | Frakes et al. ................. | 382/128 |
| 2005/0163357 | A1 * | 7/2005 | Makram-Ebeid et al. .... | 382/128 |
| 2007/0014453 | A1 * | 1/2007 | Nowinski et al. ............. | 382/128 |
| 2007/0031019 | A1 * | 2/2007 | Lesage et al. ................. | 382/131 |
| 2007/0116332 | A1 * | 5/2007 | Cai et al. ...................... | 382/128 |
| 2007/0160277 | A1 * | 7/2007 | Slabaugh et al. ............. | 382/128 |
| 2007/0248260 | A1 * | 10/2007 | Pockett ......................... | 382/154 |
| 2008/0170763 | A1 * | 7/2008 | Begelman et al. ............ | 382/128 |
| 2008/0205722 | A1 * | 8/2008 | Schaefer et al. ............. | 382/128 |
| 2009/0028403 | A1 * | 1/2009 | Bar-Aviv et al. ............. | 382/128 |

OTHER PUBLICATIONS

Aylward, Stephen R., "Initialization, noise, singularities, and scale in height-ridge traversal for tubular object centerline extraction", *IEEE Trans. on Medical Imaging*, vol. 21, No. 2, Feb. 2002, 21(2):61-75.
Comaniciu, Dorin, et al., "Mean shift: A robust approach toward feature space analysis", *IEEE Trans. PAMI*, 24(5):603-619, 2002, 603-619.
Deschamps, Thomas, et al., "Fast extraction of minimal paths in 3d images and applications to virtual endoscopy", *Medical Image Analysis*, 5(4):281-299, 2001, 281-299. Frangi, Alejandro F., et al., "Multiscale vessel enhancement filtering", *Lecture Notes in Computer Science*, vol. 1496, 1998, 130 and following.
Krissian, Karl, et al., "Model based detection of tubular structures in 3D images", *Computer Vision and Image Understanding*, 80(2):130-171, Nov. 2000, 130-171.
Nain, Delphine, et al., "Vessel segmentation using a shape driven flow", *Proceedings of MICCAI*, St. Malo, France, pages 51-59, 2004, 51-59.
Siddiqi, Kaleem, et al., "3D flux maximizing flows", *Energy Minimizaton Methods in Computer Vision and Pattern Recosnition*, 2001, 636-650.
Wong, Wilbur C., et al., "Augmented vessels for pre-operative preparation in endovascular treatments", *MICCAI*, pp. 602-609, 2004, 602-609.

* cited by examiner

*Primary Examiner* — Jack Berman
*Assistant Examiner* — Jason McCormack
(74) *Attorney, Agent, or Firm* — Donald B. Paschburg

(57) ABSTRACT

Methods and systems for modeling cerebral aneurysm and their incoming and outgoing vessels from 3D image data are disclosed. Aneurysms and vessels are segmented from their background using a graph-cuts method. Begin and end of vessels are determined. Construction of a centerline of the incoming and outgoing vessels using a measure of vesselness in calculating a minimum cost path in a graph with nodes being representation of pixels is also disclosed. Vessel surface models are constructed from sub-voxel cross-sectional segmentation. The interpolation of vessels inside an aneurysm based on smooth continuity is disclosed. Selection of endovascular stents based on interpolation results is also provided.

16 Claims, 10 Drawing Sheets

MODELING CEREBRAL ANEURYSMS IN MEDICAL IMAGES

CROSS-REFERENCE TO RELATED APPLICATIONS

This application claims the benefit of U.S. Provisional Application No. 60/909,724 filed Apr. 3, 2007, which is incorporated herein by reference.

BACKGROUND OF THE INVENTION

The present invention relates to segmentation and visualization of blood vessels in image data. In particular it relates to modeling of cerebral aneurysms and incoming and outgoing vessels from 3D image data.

Cerebral aneurysms are the enlargements of arteries, which often tend to occur at or near bifurcations of arteries of the brain. In recent years, non-invasive treatment of cerebral aneurysms has become popular due to the advances in image acquisition devices. In clinical settings, threshold based segmentation algorithms or maximum intensity projection (MIP) visualizations combined with user interactions are heavily used for the treatment planning of cerebral aneurysms.

Unfortunately, these techniques are often sensitive to parameter settings, and may adversely affect the accuracy of the results to be used in treatment planning. Parameter setting is also not user friendly. Accordingly, novel and improved post-processing applications and methods for modeling aneurysms and their vessels are required for such treatment planning.

SUMMARY OF THE INVENTION

One aspect of the present invention presents a novel method and system for modeling aneurysms in blood vessels.

In accordance with another aspect of the present invention, a method is provided for modeling a cerebral vessel with a beginning and an end with an aneurysm from image data having a plurality of image pixels, comprising segmenting of the aneurysm and cerebral vessel from a background into a segmentation mask, determining the beginning and the end of the cerebral vessel, extracting the local centerline of the cerebral vessel up to the aneurysm, and constructing a 3D cerebral vessel surface model up to the aneurysm.

In accordance with a further aspect of the present invention, a method for modeling a cerebral vessel is provided wherein the aneurysm and cerebral vessel are segmented from the background into a segmentation mask by comprising the steps of: limiting the segmentation process to image data within a bounding box, placing an initial seed inside the aneurysm and parental vessels, and applying graph-cuts optimization originating from the seed to create a segmentation mask for the aneurysm and cerebral vessel.

In accordance with another aspect of the present invention, a method is provided for modeling a cerebral vessel wherein constructing the 3D cerebral vessel surface model up to the aneurysm includes the steps of constructing a plurality of cerebral vessel sub-voxel 2D cross-sectional contours at a plurality of locations of the local center axis of the cerebral vessel, and constructing a 3D vessel surface model from the plurality of 2D contours.

In accordance with a further aspect of the present invention, a method for modeling a cerebral vessel is provided wherein the beginning and the end of the cerebral vessel are determined from an intersection of the segmentation mask and the bounding box.

In accordance with another aspect of the present invention, a method for modeling a cerebral vessel is provided further comprising constructing an approximate aneurysm mask by applying a constrained distance transform starting from aneurysm medialness points.

In accordance with a further aspect of the present invention, a method for modeling a cerebral vessel is provided wherein the extracting of the centerline includes the steps of defining a measure of vesselness of the plurality of image pixels creating a graph of nodes and edges wherein nodes represent pixels in the plurality of pixels and assigning a cost to an edge, the cost of an edge being determined as a measure of vesselness calculated orthogonal to the edge, and determining the local center axis by calculating a minimal-cost path in the graph.

In accordance with another aspect of the present invention, a method for modeling a cerebral vessel is provided wherein the measure of vesselness VM(x,y,z) for a pixel at coordinate (x,y,z) is related to a fit measure $f_i$ along a ray for a number of N rays according to an expression $$VM(x, y, z) = \frac{1}{\sum_{i=1}^{N} f_i}.$$

In accordance with a further aspect of the present invention, a method for modeling a cerebral vessel is provided wherein a fit measure $f_i$ along a ray is a difference between a measured intensity profile I and a vessel model V according to an expression $$f_i = \operatorname{argmin}_{R,\sigma} \left( \begin{array}{c} \gamma_1 \sum_{x=0}^{R} \|V_i(x, R, \sigma) - I_i(x)\|^2 f(x) + \\ \gamma_2 \sum_{x=R}^{x_B} \|V_i(x, R, \sigma) - I_i\|^2 + \gamma_3 \sum_{x=x_B}^{x_E} \|V_i(x, R, \sigma) - I_i(x)\|^2 g(x) \end{array} \right).$$

In accordance with another aspect of the present invention, a method for modeling a cerebral vessel is provided further comprising completing the centerline through the aneurysm by using interpolation completing the 3D vessel surface through the aneurysm, and modeling the aneurysm and parental vessels as separate objects in an image.

In accordance with a further aspect of the present invention, a method for modeling a cerebral vessel is provided wherein the interpolation is a bi-spline interpolation between two end points of vessels.

In accordance with another aspect of the present invention, a method for modeling a cerebral vessel is provided further comprising selecting an endo-vascular stent based on the interpolation.

In accordance with a further aspect of the present invention, a system for modeling a cerebral vessel with a beginning and an end with an aneurysm from image data having a plurality of image pixels is provided comprising a processor, and software operable on the processor to perform the steps of the methods provided herein as aspects of the present invention.

DESCRIPTION OF A PREFERRED EMBODIMENT

Figure 1:
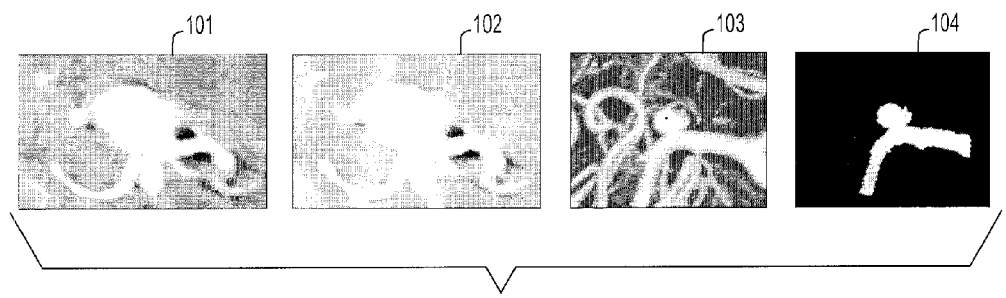
FIG. 1 illustrates the segmentation of aneurysms and parental vessels in accordance with an aspect of the present invention.

A new method for modeling aneurysms and their vessels, for instance, from 3D X-ray, MRA and subtraction CTA data via a single seed placement inside an aneurysm will be provided. A new method based on the principles of edge based graph cuts will be provided for the segmentation of aneurysms and their parental vessels, which delineates the boundary between vascular structures (aneurysms and vessels) and background accurately. However, when vascular structures are close to each other, they cannot be well separated due to the presence of strong partial voluming effects. As an aspect of the present invention, vessels will be accurately modeled up to aneurysms. A new framework for the extraction of center-axis representation as well as explicit vessel surface models from for instance 3D-X Ray, CTA/MRA data is provided. In this framework, local vessel-axis models are extracted by an algorithm which uses cross-sectional boundary models in a graph based optimization. The surface models of vessels can be constructed by 2D cross-sectional models.

This new vessel modeling algorithm is successful for modeling vessel centerline and surfaces starting from automatically detected end points up to aneurysms. Since cerebral aneurysm interactions with vessels can change significantly, it is believed that vessel modeling inside an aneurysm should not be obtained from data but instead should be constructed by the vessel information contained up to the aneurysm. As an aspect of the present invention, an interpolating centerline and surface models between vessel end points will be provided. The smoothness energy along the interpolating centerline model is used for selecting right bridging. In addition, the user may also intervene with the process of bridging vessels if incorrect vessels are linked. The aneurysm volume and its geometric properties are then automatically obtained and used in treatment planning. In addition, the solution for interpolating vessels inside an aneurysm here provided as an aspect of the present invention can be used in selecting right endo-vascular stents, if they are to be placed in addition to coils.

Segmentation of Aneurysms and Parental Vessels

In general, segmentation of cerebral aneurysms and their feeding vessels appears to be an easy task compared to the segmentation of other medical structures since they can be visualized clearly via maximum intensity projection (MIP). In fact, region growing can achieve good results if the threshold is chosen properly. However, determination of the right threshold can be difficult due to the presence of diffused boundaries. Previously, several techniques have been proposed for the segmentation of cerebral aneurysms, for instance, in: "D. Wilson and J. Noble. Segmentation of cerebral vessels and aneurysms from mr angiography data. In *IPMI*, pages 423-428, 1997"; "E. Bullitt, S. Aylward, A. Liu, J. Stone, S. K. Mukherjee, C. Coey, G. Cerig, and S. M. Pizer. 3d graph description of the intracerebral vasculature from segmented MRA and tests of accuracy by comparison with X-ray angiograms. In *IPMI*, pages 308-321, 1999"; "G. S. Monica Hernandez, Alejandro F. Frangi. Non-parametric region-based information and implicit deformable models: Method and evaluation. In *MICCAI*, pages 594-602, 2003"; and in "W. C. Wong, A. C. Chung, and S. C. Yu. Augmented vessels for pre-operative preparation in endovascular treatments. In *MICCAI*, pages 602-609, 2004". A technique based on the principles of graph cuts for determining such threshold which guarantees the segmentation boundaries coincide with the edges will be provided as an aspect of the present invention.

A technique is provided as an aspect of the present invention that is based on iterative region growing from a seed point whose convergence criteria are determined from maximum average gradient cut along a detected boundary. It is assumed that the surface of an aneurysm and the surrounding vessels are represented by N connected voxels. In 3D rotational X-ray or MRA data, such surfaces pass through the highest gradient points. In other words, one seeks to obtain a surface which maximizes the average gradient among all possible solutions. Mathematically, the maximum average gradient cut for a surface with N points can be computed as $$\frac{\sum_{i=1}^{N} |\nabla I_i|}{N}.$$

Herein I represent an image. Traditionally, graph cuts optimization techniques are popular for computing minimum total gradient. However, computing minimum average gradient cut is not possible with these algorithms. Based on the experiences of the inventors, maximum gradient, instead of average gradient, does not always produce the desired solution since it is size dependent.

Instead of using an optimization algorithm, all possible solutions are detected via a region growing algorithm by reducing the thresholds from the maximum possible intensity value to minimum intensity value by computing their average gradient. Since aneurysms occupy a small area of an image, this algorithm is applied in a cropped volume. It should be noted that this segmentation algorithm is capable of detecting boundaries between vascular structure (vessels and aneurysm) and background very accurately. However, if a vessel is very close to another vessel or an aneurysm its correct boundaries may not be computed reliably due to the partial voluming effects. As an aspect of the present invention, vessels up to aneurysms are modeled in great detail with a new centerline and vessel surface detection algorithm as will be provided below. FIG. 1 shows the segmentation of aneurysm and its vessels with the provided algorithm from a single seed point in the three images 101, 102, 103 and 104.

This segmentation mask is used to find the beginning and end of vessels which are then accurately constructed. Discrete medialness representation, shape reconstruction from medialness points and the user placed seed point are used to achieve these goals. Medialness points of an aneurysm and vessels are detected from the distance transform of the segmented volume by voxels which have distance value greater than (or equal to) all neighbors' distance. In other words, medialness voxels correspond to the voxels which receive only the incoming distance propagations.

Figure 2:
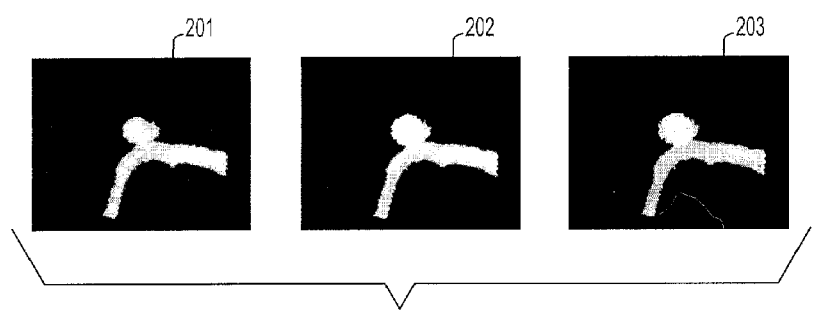
FIG. 2 provides images of vessels and aneurysms in accordance with aspects of the present invention.

Now referring to FIG. 2, wherein image 201 shows the medialness points of a segmentation mask; image 202 shows the approximate reconstruction of the aneurysm mask; and image 203 shows the detection of end points of the parent vessels.

Image 201 in FIG. 2 shows these medialness points of the segmentation mask. These medialness points are classified as vessel or aneurysm based on the distance value and the user placed seed point. The approximate aneurysm mask can be constructed via constrained distance transform starting from aneurysm medialness points. It should be observed that contour based distance transforms, which starts from the seed point, are stopped when the maximum distance contained at the initial seed point is reached. It may be enough to mark an aneurysm with a sphere if the aneurysm has a single medialness point. In practice, aneurysms often contain more than one medialness point since they are more elliptical in shape. Thus, contour based distance transforms are very suitable for the reconstruction. Image 202 in FIG. 2 shows the reconstructed aneurysms with this algorithm. The end points of vessels where the accurate tracking algorithm starts are determined from the intersection of segmentation mask and the bounding box, as illustrated in image 203 of FIG. 2. Below, a new method will be presented for tracking the vessel centerline from the beginning points up to the aneurysm mask reconstructed by the constrained distance transform.

Robust Vessel Centerline and Surface Modelling

There is a broad variety of vessel segmentation and modeling algorithms ranging from simple thresholding and region growing to more complex deformable model techniques, modeling vessels directly from images, such as described in "D. Wilson and J. Noble. Segmentation of cerebral vessels and aneurysms from mr angiography data. In *IPMI*, pages 423-428, 1997", etc. Traditionally, vessels binary masks are often created by a vessel segmentation algorithm, such as described for instance in "K. Siddiqi and A. Vasilevskiy. 3d flux maximizing flows. In *International Workshop on Energy Minimizing Methods In Computer Vision*, 2001" and in "D. Nain, A. Yezzi, and G. Turk. Vessel segmentation using a shape driven flow. In *MICCAI*, 2004" and their centerline models are extracted by shortest paths algorithms operating on this vessel mask, such as described in "T. Deschamps and L. Cohen. Fast extraction of minimal paths in 3d images and applications to virtual endoscopy. *Medical Image Analysis*, 5(4):281-299, 2001". Alternatively, vessel centerlines can be constructed directly from images by the use of vesselness, such as described in "A. F. Frangi, W. J. Niessen, K. L. Vincken, and M. A. Viergever. Multiscale vessel enhancement filtering. In *MICCAI*, pages 82-89, 1998"; in "K. Krissian, C. Malandain, N. Ayache, R. Vaillant, and Y. Trousset. Model based detection of tubular structures in 3d images. *Computer Vision and Image Understanding*, 80(2):130-171, November 2000"; in "O. Wink, W. J. Niessen, and M. A. Viergever. Multiscale vessel tracking. *IEEE Trans. on Medical Imaging*, 23(1):130-133, 2004"; and in "J. A. Tyrrell, E. di Tomaso, D. Fuja, R. Tong, K. Kozak, E. B. Brown, R. Jain, and B. Roysam. Robust 3-d modeling of vasculature imagery using superellipsoids. *IEEE Transactions on Medical Imaging*, 2006" or by medialness filters as described in "S. Aylward and E. Bullitt. Initialization, noise, singularities, and scale in height-ridge traversal for tubular object centerline extraction. *TMI*, 21(2):61-75, 2002".

Figure 3:
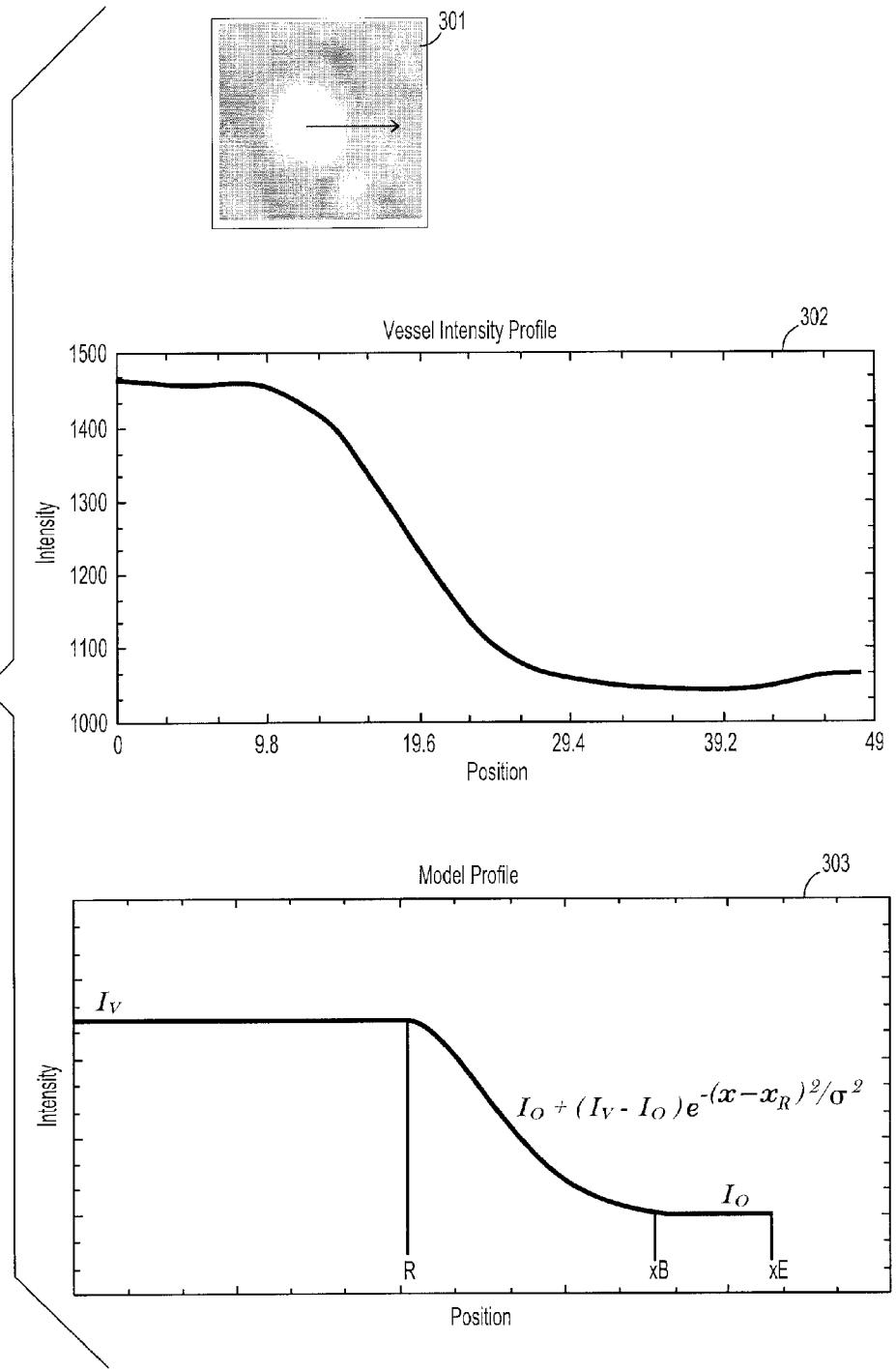
FIG. 3 illustrates the concept of vesselness in accordance with another aspect of the present invention.

As an aspect of the present invention, a novel technique is provided for computing a vesselness measure which is based on multi-scale cross-sectional vessel modeling. Blood vessels in CTA/MRA have typically circular/elliptic shapes in cross-sectional views even though local variations are not too uncommon due to the presence of nearby vessels or pathologies. Ideally, a 2D cross-sectional vessel profile consists of a circular/elliptic bright disk and darker ring around it. FIG. 3 image 301 shows a typical vessel in cross-sectional view. The vesselness measure provided here uses a circularity assumption and intensity profile. Rays from the center point are initialized and intensity profile collected along them. The typical intensity profile of a vessel and its immediate background along a ray starting from the center is shown in graph 302 of FIG. 3. This 1D vessel intensity model is further divided into three intervals, $R_1$, $R_O$, $R_B$.

As shown in FIG. 3 graph 303, the inside region of a vessel along a ray $R_1$, can be represented by a bright intensity region whose size depends on the size of the vessel. Similarly, the outside region of a vessel along a ray $R_O$ can be represented by a dark intensity region whose size depends on the presence of nearby structures. The boundary region between vessel and background $R_B$, can be described by a Gaussian profile. Mathematically, the vessel intensity model along a ray is $$V(x, R, \sigma) = \begin{cases} I_V & \text{if } x \geq 0 \text{ and } x < R \\ I_O + (I_V - I_O)e^{-(x-R)^2/\sigma^2} & \text{if } x \geq R \text{ and } x < x_B \\ I_O & \text{if } x \geq x_B \text{ and } x < x_E. \end{cases} \quad (1)$$

Herein R is the radius and $I_V$ and $I_O$ are the intensity values representing inside and outside a vessel, respectively. Intensity data, I obtained from original CTA/MRA data along a ray should match the profile of the 1-D intensity vessel model V if the observed data I is obtained from a vessel. The difference between the measured intensity profile I and vessel model V is used as a fit measure in the vesselness criteria. i.e. the fit measured $f_i$ along a ray, is given by $$f_i = \operatorname{argmin}_{R,\sigma} \begin{pmatrix} \gamma_1 \sum_{x=0}^{R} \|V_i(x, R, \sigma) - I_i(x)\|^2 f(x) + \\ \gamma_2 \sum_{x=R}^{x_B} \|V_i(x, R, \sigma) - I_i\|^2 + \\ \gamma_3 \sum_{x=x_B}^{x_E} \|V_i(x, R, \sigma) - I_i(x)\|^2 g(x) \end{pmatrix}. \quad (2)$$

Herein $f(x)=u(I_V-I(x))$, $g(x)=u(I(x)-I_O)$ and $u(x)$ is a step function. $y_1$, $y_2$ and $y_3$ are the weights for the different intervals. Observe that calcifications are not modeled separately and they are included inside vessels via the use of f(x). Similarly, very dark regions such as air in lungs are included in background representation via g(x). Then the vesselness measure VM(x, y, z) of a point is given from the summation of such fit measures along all rays, i.e., $$VM(x, y, z) = \frac{1}{\sum_{i=1}^{N} f_i},$$

where N is the total number of rays.

Observe that the vessel intensity model contains two important values namely, $I_V$ and $I_O$, which fundamentally correspond to the minimum brightness value of vessels and the maximum darkness value of surrounding structures. In one embodiment of implementation, these values are locally estimated in great accuracy by computing 2D cross-sectional boundaries in many directions and using the one that gives the best fit to an elliptic Fourier descriptor. This algorithm detects 2D boundaries and classifies the intensities of vessel and its surroundings via multi-scale mean shift filtering as described in "D. Comaniciu and P. Meer. Mean shift: A robust approach toward feature space analysis. IEEE Trans. PAMI, 24(5):603-619, 2002". Mean-shift filtering produces discontinuity preserving smoothing which then specifies $I_V$ and $I_O$.

Figure 4:
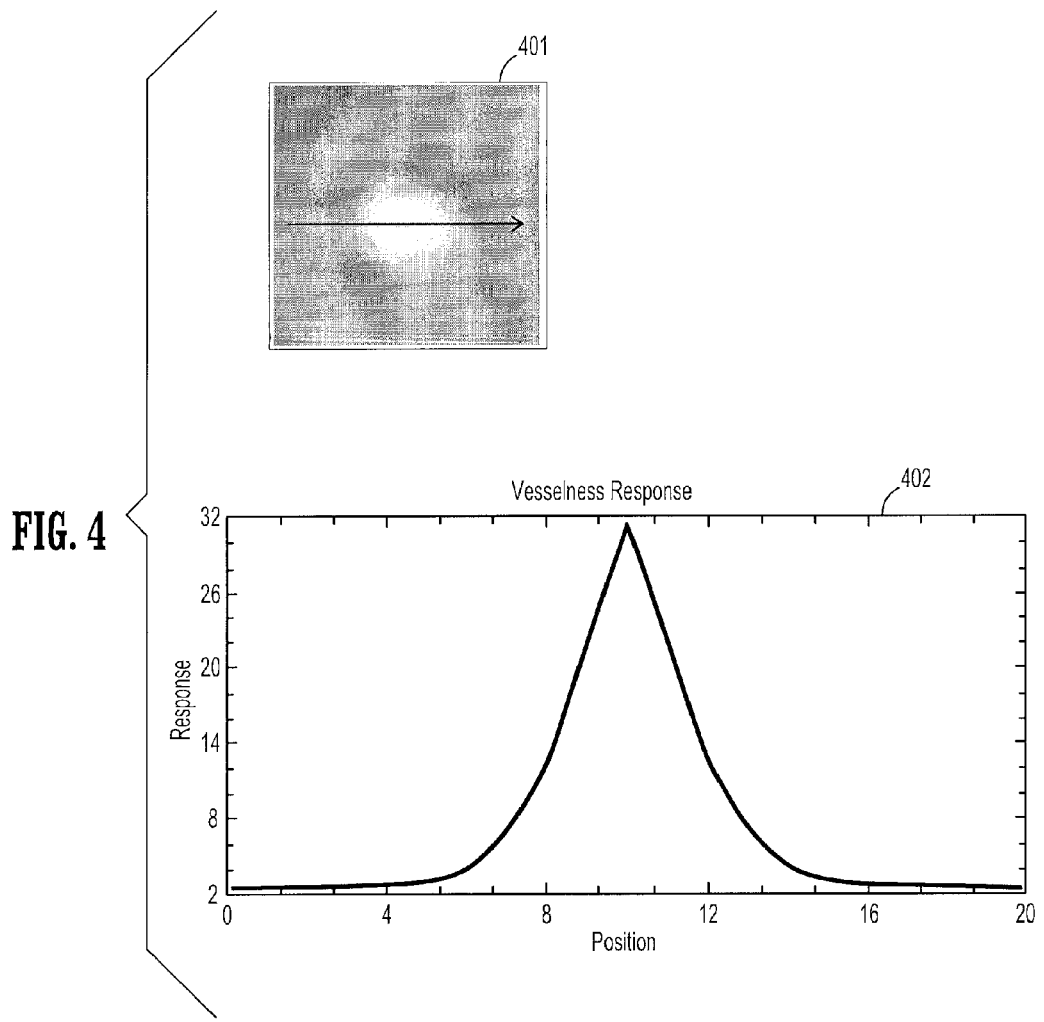
FIG. 4 is another illustration of the concept of vesselness in accordance with an aspect of the present invention.
Figure 5:
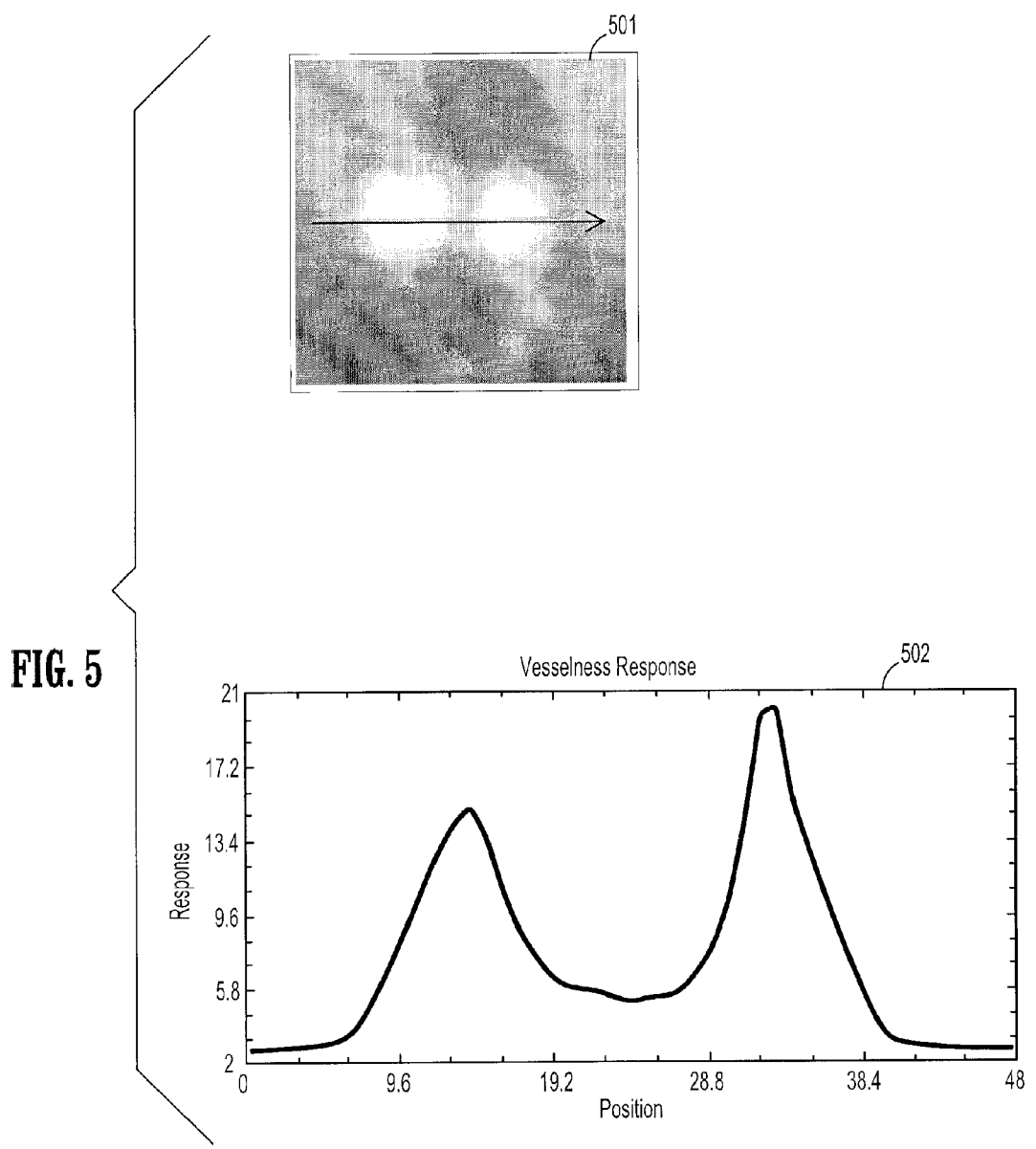
FIG. 5 is yet another illustration of the concept of vesselness in accordance with an aspect of the present invention.

The technique herein provided as an aspect of the present invention has two major contributions: First, its response characteristics are very close to the ones that may be expected from an ideal vesselness filter. The provided vesselness measure gives strong responses at the center of a vessel and response drops rapidly towards vessel boundaries and very small responses are obtained in non-vascular areas. This is shown in FIG. 4 image 401 and vesselness response graph 402. Also, the presence of a bright structure does not have a strong impact on the responses. Unlike Hessian based techniques, the herein provided approach gives a very low response between two nearby vessels which may then result in better separation of nearby vessels via segmentation algorithms using such measures. This is shown in FIG. 5 in image 501 and vesselness graph 502.

Figure 6:
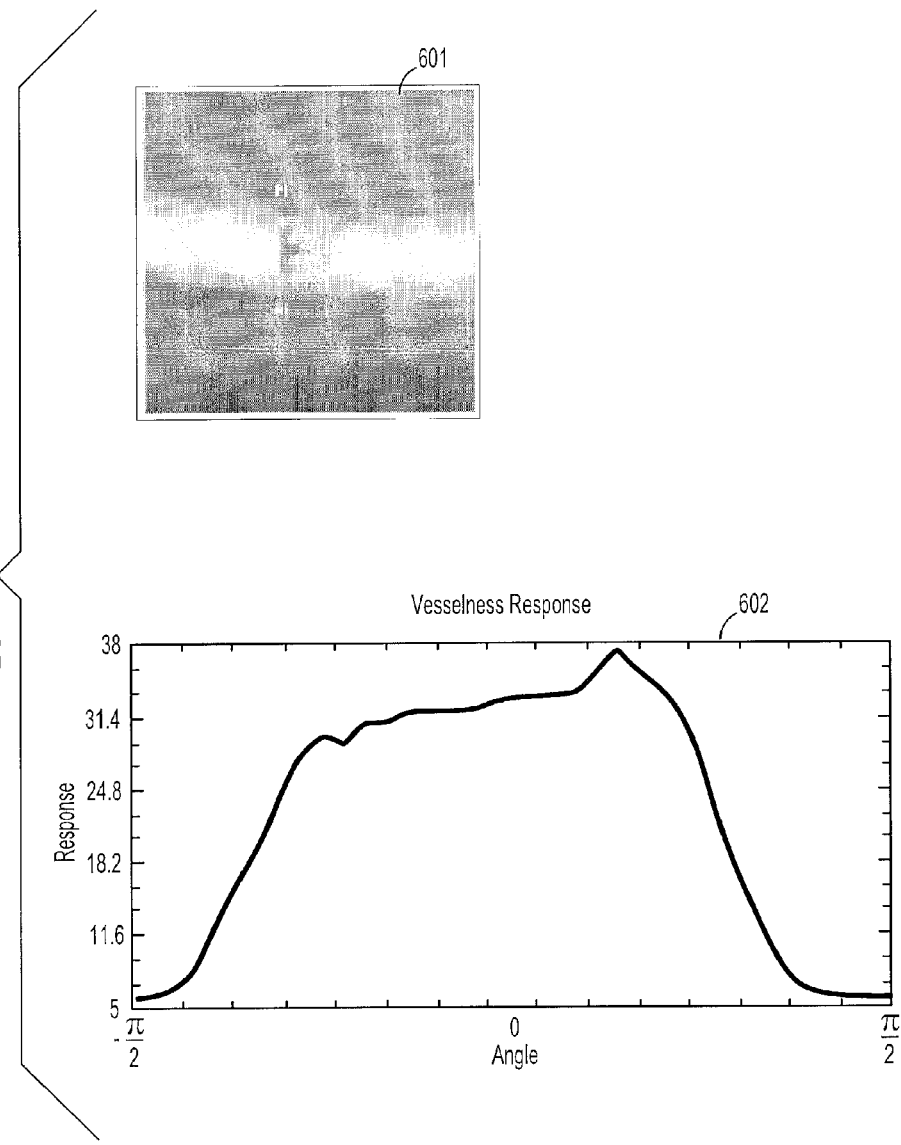
FIG. 6 is yet another illustration of the concept of vesselness in accordance with an aspect of the present invention.

Second, the herein applied technique does not require the estimation of vessel direction. Other techniques may use the eigenvectors of the Hessian to determine the vessel direction. However, bright structures close to the vessel of interest can erroneously affect the direction of a vessel, and thus vesselness measure, as well. The herein applied filtering technique produces very good responses when results are computed from orthogonal planes. The response drops rapidly when results are computed from oblique plane. FIG. 6 illustrates in image 601 and graph 602, the dependency of the vesselness response on different orientations. A high response is obtained until 45 degrees when the vessel in the cutting plane starts to deviate significantly from the cross-sectional model. This is in agreement with an ideal vesselness filter.

Figure 7:
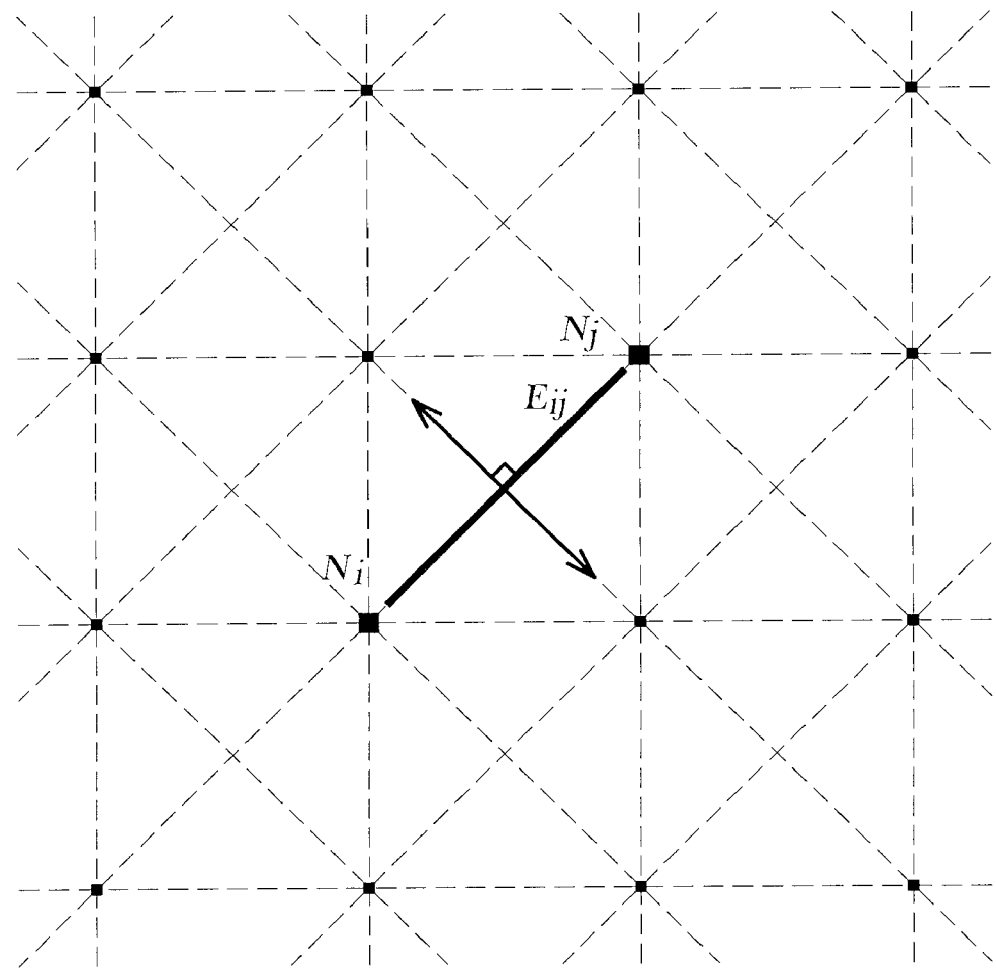
FIG. 7 illustrates a discrete graph in accordance with an aspect of the present invention.

Next, an algorithm for extracting a local center-axis representation of vessels accurately and quickly, will be provided. The approach is based on a graph-based minimum cost path (or front propagation) detection algorithm which operates on vesselness map obtained from the algorithm provided above. Let G=(N. E) be a discrete graph where N and E represent nodes and edges, respectively. In general, Dijkstra's shortest paths are very popular in finding minimum-cost path between a source $N_s$ and a goal $N_g$. The cost of edges C(E) are chosen to be the vesselness measure, i.e., $C(E_i)=1.0/VM(E_i)$. The vesselness measure of a graph edge is computed in orthogonal to that edge. This is illustrated in FIG. 7 showing a discrete graph wherein the vesselness filters are applied orthogonal to its edges. In summary, Dijkstra's algorithm (or front propagation algorithm) propagates fronts in discrete domain and assigns the minimum accumulative cost measure to nodes φ(N) and keeps the history of propagation from the source to the goal H(N) which is used in constructing the minimum cost path. This propagation terminates when the propagation reaches the goal node, $N_g$. The minimum cost path between source and goal can be easily detected from the history map, H.

Figure 8:
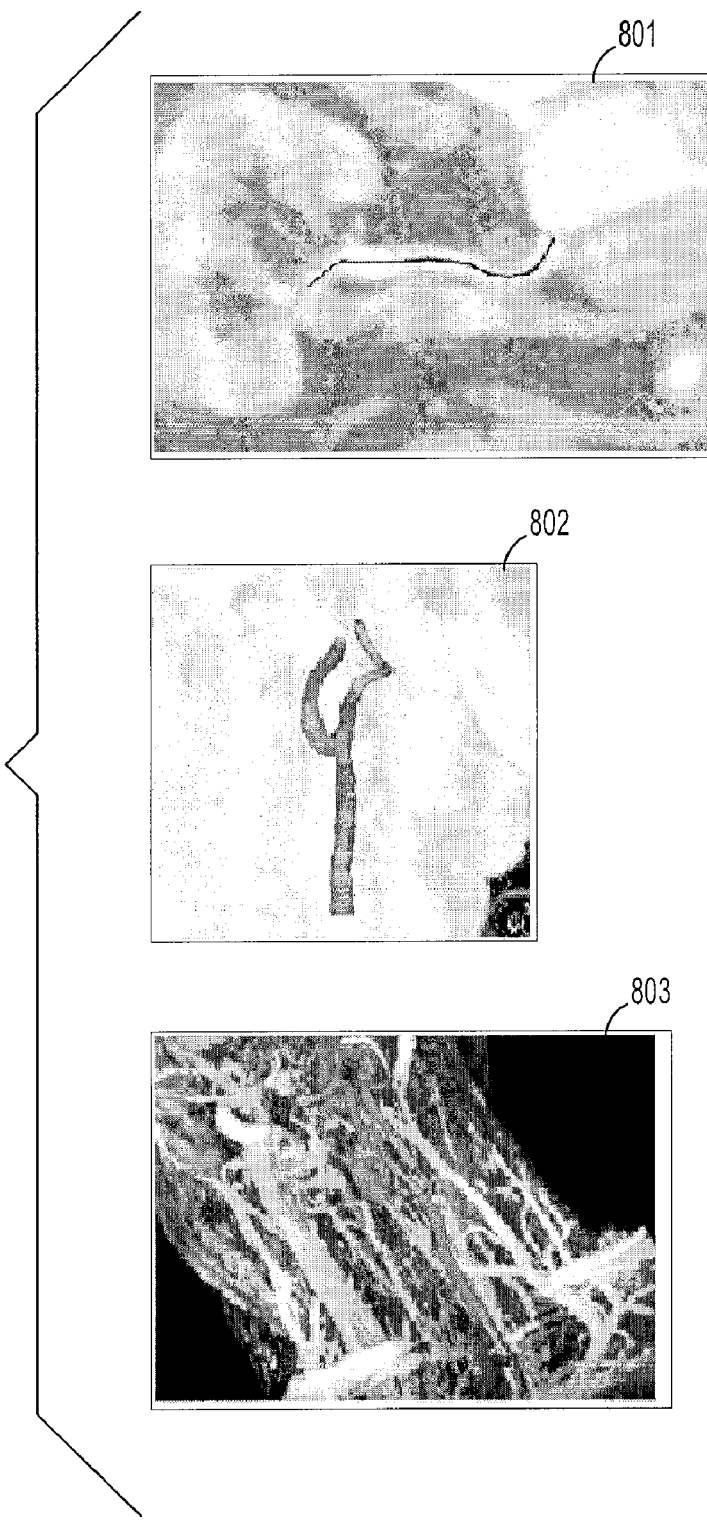
FIG. 8 illustrates local center axis models in accordance with an aspect of the present invention.

The major contribution of this minimum cost path finding algorithm is the use of vesselness measure as the cost of edges E and its orthogonal computation to the edges. This is illustrated in FIG. 7. In fact, this orthogonal computation is the key factor for great accuracy and computational efficiency since the costs obtained on vessel cross-sections are very small. FIG. 8 image 801 illustrates the centerline obtained between two seeds from this algorithm.

In addition to the vessel centerlines, construction of the vessel surface models by sub-voxel 2D cross-sectional models is provided. This method of vessel surface construction is described in U.S. patent application Ser. No. 11/684,694 filed on Mar. 12, 2007 and U.S. patent application Ser. No. 11/399, 164 filed on Apr. 6, 2006 which are both incorporated herein by reference in their entirety. By applying this method, subvoxel accurate vessel cross-sectional boundaries are constructed at several locations of a given centerline model. A 3D vessel surface model is then constructed from these 2D contours. Successive 2D contours are used to construct the local triangulation surface by finding the corresponding points of each contour, i.e., points that are closest to each other. FIG. 8 image 802 illustrates the surface models constructed from the center line models.

Vessel Completion Via Smoothness Continuity

The herein provided vessel centerline and surface modeling technique as an aspect of the present invention is very well suited for modeling cerebral vessels up to aneurysms as is shown in images 801, 802 and 803 of FIG. 8. However, the presence of an aneurysm makes vessels deviate from tubular structures, thus the modeling approach should not be used at such places where it is quite difficult to distinguish vessels and aneurysms. Enlargement in a vessel due to the formation of an aneurysm may affect only a small part of the vessel, which may be accurately modeled by segmentation algorithms. However, when aneurysms form at the bifurcations, or when they surround vessels significantly, vessel model extraction should not depend on the data inside an aneurysm. The centerline and surface models are tracked up to aneurysms and interpolation is used between these end points instead of tracking them with original data. In recent coil treatments, endo-vascular stents are often inserted between vessels to minimize the dislocation of coils over time. Thus, the here provided technique can also help the user in selecting the right stent.

Figure 9:
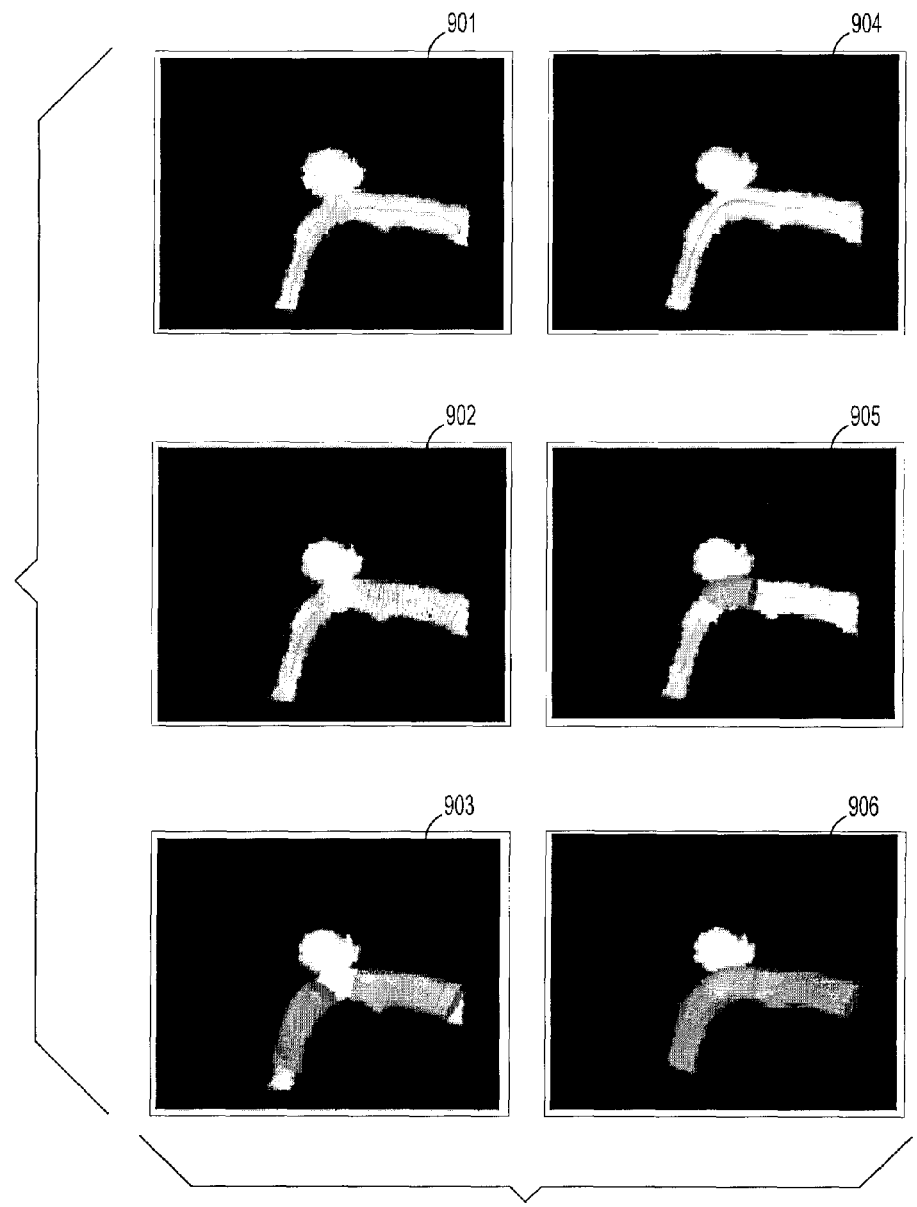
FIG. 9 illustrates the modeling of vessels in accordance with an aspect of the present invention.

Based on experiments, bi-spline interpolation of centerline and cross-sectional boundaries between two end points of vessels are quite successful. When there are more than two end points for an aneurysm which often form at a bifurcation, one can combinatorialy compute the interpolating centerline between all end points. As an aspect of the present invention, the completion energies of the interpolating splines are used to decide which end points to bridge. The total curvature variation is used as the completion energy. The minimum energy (smoothest) splines are selected for the correct vessel construction. In general, this works very well in practice. The user is provided with the opportunity to make such selection by simply selecting such interpolating curves of which examples are shown in FIG. 9. FIG. 9 illustrates the modeling of vessels in the presence of cerebral aneurysm. Herein image 901 illustrates accurate centerline extraction from the end points of a vessel up to the aneurysm; 902 illustrates 2D cross-sectional modeling along the center-lines; 903 illustrates 3D surface models constructed from the 2D contours; 904 illustrates completion curves between the end points of vessels via bi-splines; 905 illustrates a completed surface for the vessels; and image 906 illustrates modeling an aneurysm and its parental vessels.

In this disclosure, the term "pixel" is used to indicate a data structure that is used to compose an image. Although the term may indicate a two-dimensional element, for purposes of the following disclosure, "pixel" is also intended to include three-dimensional picture elements, i.e., voxels. The use of the word "node" shall be understood to refer to either pixel or voxel.

Results

Figure 10:
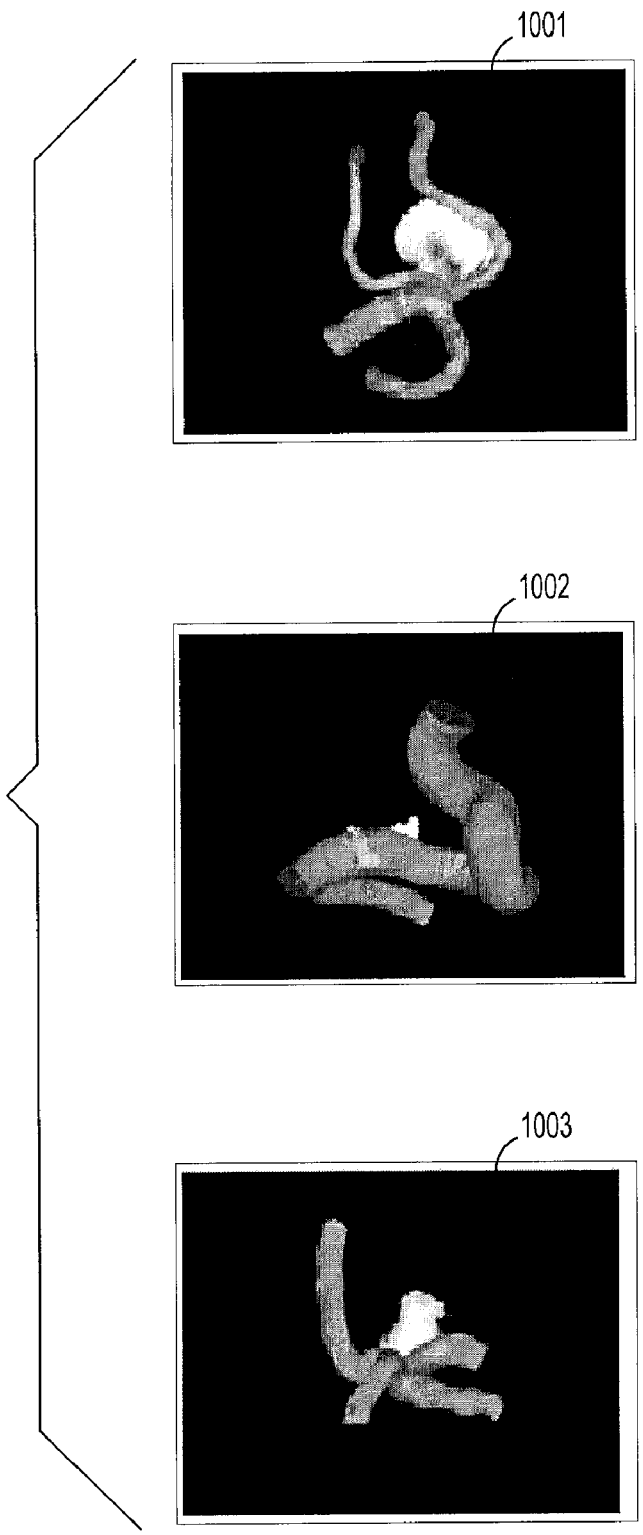
FIG. 10 illustrates results obtained from applying one or more aspects of the present invention.

The here provided algorithm was successfully tested on 8 data set containing cerebral aneurysms and provided results as shown in FIG. 10 in images 1001, 1002 and 1003. In an experiment, the user placed a single seed inside aneurysms and the algorithm was capable of producing results in less than 10 seconds on 2.8 GHz PC. Similarly, the vessel centerline and surface modeling algorithm has been successfully tested on more than 50 CTA/MRA data sets. Accordingly, a successful single click method for modeling cerebral aneurysm in, for instance, 3D X-Ray, MRA and subtraction CTA, which has been recently introduced.

System

Figure 11:
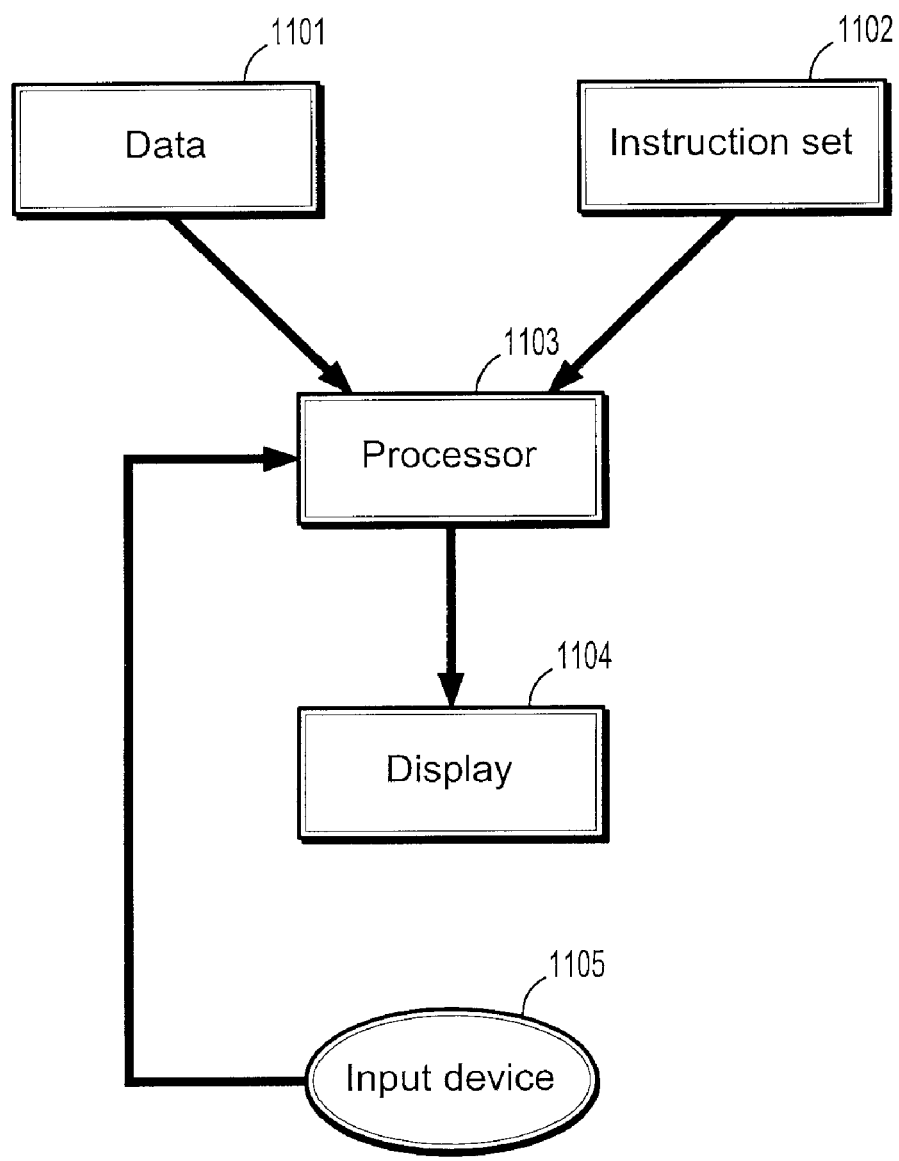
FIG. 11 illustrates a computer system that is used to perform the steps described herein in accordance with another aspect of the present invention.

The methods that are aspects of the present invention can be executed by a system as shown in FIG. 11. The system is provided with data 1101 representing image data. An instruction set or program 1102 executing the methods of the present invention is provided and combined with the data in a processor 1103, which can process the instructions of 1102 applied to the data 1101. A processed image can be outputted on a device 1104. Such a device can be a display. The processor can be dedicated hardware. However, the processor can also be a CPU or any other computing device that can execute the instructions of 1102. An input device 1105 like a mouse, or track-ball or other input device may be present to allow a user to select an initial object or place a seed. Accordingly the system as shown in FIG. 11 provides a system for modeling cerebral aneurysms in images using methods disclosed herein.

The following references are generally descriptive of the background of the present invention and are hereby incorporated herein by reference: [1]. S. Aylward and E. Bullitt. Initialization, noise, singularities, and scale in height-ridge traversal for tubular object centerline extraction. *TMI*, 21(2): 61-75, 2002. [2]. E. Bullitt, S. Aylward, A. Liu, J. Stone, S. K. Mukherjee, C. Coey, G. Cerig, and S. M. Pizer. 3d graph description of the intracerebral vasculature from segmented MRA and tests of accuracy by comparison with X-ray angiograms. In *IPMI*, pages 308-321, 1999. [3]. D. Comaniciu and P. Meer. Mean shift: A robust approach toward feature space analysis. *IEEE Trans. PAMI*, 24(5):603-619, 2002. [4]. T. Deschamps and L. Cohen. Fast extraction of minimal paths in 3d images and applications to virtual endoscopy. *Medical Image Analysis*, 5(4):281-299, 2001. [5]. A. F. Frangi, W. J. Niessen, K. L. Vincken, and M. A. Viergever. Multiscale vessel enhancement filtering. In *MICCAI*, pages 82-89, 1998. [6]. K. Krissian, C. Malandain, N. Ayache, R. Vaillant, and Y. Trousset. Model based detection of tubular structures in 3d images. *Computer Vision and Image Understanding*, 80(2): 130-171, November 2000. [7]. G. S. Monica Hernandez, Alejandro F. Frangi. Non-parametric region-based information and implicit deformable models: Method and evaluation. In *MICCAI*, pages 594-602, 2003. [8]. D. Nain, A. Yezzi, and G. Turk. Vessel segmentation using a shape driven flow. In *MICCAI*, 2004. [9]. K. Siddiqi and A. Vasilevskiy. 3d flux maximizing flows. In *International Workshop on Energy Minimizing Methods In Computer Vision*, 2001. [10]. J. A. Tyrrell, E. di Tomaso, D. Fuja, R. Tong, K. Kozak, E. B. Brown, R. Jain, and B. Roysam. Robust 3-d modeling of vasculature imagery using superellipsoids. *IEEE Transactions on Medical Imaging*, 2006. [11]. D. Wilson and J. Noble. Segmentation of cerebral vessels and aneurysms from mr angiography data. In *IPMI*, pages 423-428, 1997. [12]. O. Wink, W. J. Niessen, and M. A. Viergever. Multiscale vessel tracking. *IEEE Trans. on Medical Imaging*, 23(1):130-133, 2004. [13]. W. C. Wong, A. C. Chung, and S. C. Yu. Augmented vessels for pre-operative preparation in endovascular treatments. In *MICCAI*, pages 602-609, 2004.

While there have been shown, described and pointed out, fundamental novel features and aspects of the invention as applied to preferred embodiments thereof, it will be understood that various omissions, substitutions, and changes in the form and details of the system, and methods illustrated and in their operation, may be made by those skilled in the art without departing from the spirit of the invention. It is the intention, therefore, to be limited only as indicated by the scope of the claims appended hereto.

The invention claimed is:

1. A method for modeling a cerebral vessel with a beginning and an end with an aneurysm from image data having a plurality of image pixels, comprising:

a processor segmenting the aneurysm and cerebral vessel from a background into a segmentation mask;

the processor determining the beginning and the end of the cerebral vessel;

the processor extracting a local centerline between the beginning and end of the cerebral vessel up to the aneurysm by applying a measure of vesselness based on multi-scale cross-sectional vessel modeling; and the processor constructing a 3D cerebral vessel surface model up to the aneurysm wherein the extracting of the centerline includes the steps of:

creating a graph of nodes and edges wherein nodes represent pixels in the plurality of pixels and assigning a cost to an edge, the cost of an edge being determined as a measure of vesselness calculated orthogonal to the edge; and determining the local center axis by calculating a minimal-cost path in the graph;

wherein the measure of vesselness $VM(x,y,z)$ for a pixel at coordinate $(x,y,z)$ is related to a fit measure $f_i$ along a ray for a number of N rays according to an expression $$VM(x, y, z) = \frac{1}{\sum_{i=1}^{N} f_i}; \text{ and}$$

wherein a fit measure $f_i$ along a ray is a difference between a measured intensity profile I and a vessel model V according to an expression $$f_i = \text{argmin}_{R,\sigma} \left( \begin{array}{c} \gamma_1 \sum_{x=0}^{R} \|V_i(x, R, \sigma) - I_i(x)\|^2 f(x) + \\ \gamma_2 \sum_{x=R}^{x_B} \|V_i(x, R, \sigma) - I_i\|^2 + \gamma_3 \sum_{x=x_B}^{x_E} \|V_i(x, R, \sigma) - I_i(x)\|^2 g(x) \end{array} \right).$$

2. The method as claimed in claim 1, wherein the aneurysm and cerebral vessel are segmented from the background into a segmentation mask by comprising the steps:
  limiting the segmentation process to image data within a bounding box;
  placing an initial seed inside the aneurysm and parental vessels; and
  applying graph-cuts optimization originating from the seed to create a segmentation mask for the aneurysm and cerebral vessel.

3. The method as claimed in claim 1, wherein constructing the 3D cerebral vessel surface model up to the aneurysm includes the steps of:
  constructing a plurality of cerebral vessel sub-voxel 2D cross-sectional contours at a plurality of locations of the local center axis of the cerebral vessel; and
  constructing a 3D vessel surface model from the plurality of 2D contours.

4. The method as claimed in claim 2, wherein the beginning and the end of the cerebral vessel are determined from an intersection of the segmentation mask and the bounding box.

5. The method as claimed in claim 2, further comprising constructing an approximate aneurysm mask by applying a constrained distance transform starting from aneurysm medialness points.

6. The method as claimed in claim 1, further comprising:
  completing the centerline through the aneurysm by using interpolation;
  completing the 3D vessel surface through the aneurysm; and
  modeling the aneurysm and parental vessels as separate objects in an image.

7. The method as claimed in claim 6, wherein the interpolation is a bi-spline interpolation between two end points of vessels.

8. The method as claimed in claim 6, further comprising selecting an endo-vascular stent based on the interpolation.

9. A system for modeling a cerebral vessel with a beginning and an end with an aneurysm from image data having a plurality of image pixels, comprising:
  a processor;
  software operable on the processor to:
    segmenting the aneurysm and cerebral vessel from a background into a segmentation mask;
    determining the beginning and the end of the cerebral vessel;
    extracting a local centerline between the beginning and end of the cerebral vessel up to the aneurysm by applying a measure of vesselness based on multi-scale cross-sectional vessel modeling; and
    constructing a 3D cerebral vessel surface model up to the aneurysm;
  wherein the extracting of the centerline includes the steps of:
    creating a graph of nodes and edges wherein nodes represent pixels in the plurality of pixels and assigning a cost to an edge, the cost of an edge being determined as a measure of vesselness calculated orthogonal to the edge; and
    determining the local center axis by calculating a minimal-cost path in the graph;
  wherein the measure of vesselness VM(x,v,z) for a pixel at coordinate (x,y,z) is related to a fit measure $f_i$ along a ray for a number of N rays according to an expression $$VM(x, y, z) = \frac{1}{\sum_{i=1}^{N} f_i}, \text{ and}$$

wherein a fit measure $f_i$ along a ray is a difference between a measured intensity profile I and a vessel model V according to an expression $$f_i = \text{argmin}_{R,\sigma} \left( \begin{array}{c} \gamma_1 \sum_{x=0}^{R} \|V_i(x, R, \sigma) - I_i(x)\|^2 f(x) + \\ \gamma_2 \sum_{x=R}^{x_B} \|V_i(x, R, \sigma) - I_i\|^2 + \gamma_3 \sum_{x=x_B}^{x_E} \|V_i(x, R, \sigma) - I_i(x)\|^2 g(x) \end{array} \right).$$

10. The system as claimed in claim 9, wherein the aneurysm and cerebral vessel are segmented from the background into a segmentation mask, comprising the steps:
  limiting the segmentation process to image data within a bounding box;
  placing an initial seed inside the aneurysm and parental vessels; and
  applying graph-cuts optimization originating from the seed to create a segmentation mask for the aneurysm and cerebral vessel.

11. The system as claimed in claim 9, wherein constructing the 3D cerebral vessel surface model up to the aneurysm includes the steps of:
  constructing a plurality of cerebral vessel sub-voxel 2D cross-sectional contours at a plurality of locations of the local center axis of the cerebral vessel; and
  constructing a 3D vessel surface model from the plurality of 2D contours.

12. The system as claimed in claim 10, wherein the beginning and the end of the cerebral vessel are determined from an intersection of the segmentation mask and the bounding box.

13. The system as claimed in claim 10, further comprising constructing an approximate aneurysm mask by applying a constrained distance transform starting from aneurysm medialness points.

14. The system as claimed in claim 9, further comprising:
  completing the centerline through the aneurysm by using interpolation;
  completing the 3D vessel surface through the aneurysm; and
  modeling the aneurysm and parental vessels as separate objects in an image.

15. The method as claimed in claim 14, wherein the interpolation is a bi-spline interpolation between two end points of vessels.

16. The system as claimed in claim 14, further comprising selecting an endo-vascular stent based on the interpolation.

* * * * *